United States Patent [19]
Santus

[11] Patent Number: 5,952,021
[45] Date of Patent: Sep. 14, 1999

[54] STABILIZED BIOLOGICALLY ACTIVE COMPOUNDS CONTAINED IN COATED MICROGRANULES WHICH CAN BE SUSPENDED IN ALIMENTARY FLUIDS

[75] Inventor: Giancarlo Santus, Milan, Italy

[73] Assignee: Recordati S.A. Chemical and Pharmaceutical Company, Chiasso, Switzerland

[21] Appl. No.: 08/941,730

[22] Filed: Oct. 1, 1997

Related U.S. Application Data

[63] Continuation of application No. 08/458,062, Jun. 1, 1995, abandoned.

[30] Foreign Application Priority Data

Jun. 14, 1994 [IT] Italy ................................. MI94A1231

[51] Int. Cl.⁶ ...................................................... A23C 9/12
[52] U.S. Cl. ................................. 426/34; 426/42; 426/51; 426/89; 426/580; 426/599
[58] Field of Search .................... 426/34, 89, 96, 426/580, 42, 43, 49, 51, 52, 590, 599

[56] References Cited

U.S. PATENT DOCUMENTS

| | | | |
|---|---|---|---|
| 3,691,090 | 9/1972 | Kitajima | 252/316 |
| 4,218,433 | 8/1980 | Kooichi et al. | 424/15 |
| 4,786,506 | 11/1988 | Fontanelli | 424/470 |
| 5,296,236 | 3/1994 | Santus et al. | 424/490 |
| 5,464,633 | 11/1995 | Conte et al. | 424/480 |
| 5,595,762 | 1/1997 | Derrieu et al. | 424/490 |

FOREIGN PATENT DOCUMENTS

| | | |
|---|---|---|
| 0 470 572 | 2/1992 | European Pat. Off. . |
| 583726 | 2/1994 | European Pat. Off. . |
| 0 600 775 | 6/1994 | European Pat. Off. . |
| 0 601 508 | 6/1994 | European Pat. Off. . |
| 63287543 | 11/1988 | Japan . |
| 02142735 | 5/1990 | Japan . |
| 04 041 434 | 7/1990 | Japan . |
| 6-133735 | 5/1994 | Japan . |

OTHER PUBLICATIONS

D. Jones, *Drug Dev. Indus. Pharm.*, 20:3175, 1994.

*Primary Examiner*—Leslie Wong
*Attorney, Agent, or Firm*—Darby & Darby

[57] ABSTRACT

A method to protect biactive compounds and microorganisms from inactivation in the gastric tract as well as in foods. The method involves preparation and coating of a multiplicity of microgranules containing the compounds or microorganisms. The microgranules are generally smaller than 500 μm and have physical characteristics that permit homogeneous filming as well as ready suspension after coating in common foodstuffs such as milk and milk products and fruit juices.

16 Claims, No Drawings

STABILIZED BIOLOGICALLY ACTIVE COMPOUNDS CONTAINED IN COATED MICROGRANULES WHICH CAN BE SUSPENDED IN ALIMENTARY FLUIDS

This is a continuation of application Ser. No. 08/458,062, filed Jun. 1, 1995 now abandoned.

FIELD OF THE INVENTION

This invention involves ingestible materials such as foodstuffs that contain acid-labile or protease-sensitive bioactive compounds and compositions. The compounds and compositions include enzymes and microorganisms coated with a protective coating preserving the activity of said compounds and compositions within an environment that would otherwise be detrimental to said activity, said coated compounds and compositions also being capable of forming stable suspensions in various fluid and semifluid ingestible materials.

BACKGROUND OF THE INVENTION

The gastrointestinal tract of mammals and humans is populated by a complex microbiological ecosystem, commonly referred to as the intestinal flora, made up of about 400 to 500 different microbial species. The most common of these microorganisms are those belonging to the genus Bacteroides, including Bifidobacterium, Eubacterium and Fusobacterium.

The structure and function of the gastrointestinal tract and its metabolic activity are closely dependent on the presence of appropriate intestinal flora, which play a very important role in normal physiological processes and are also involved in some pathological conditions. Among other things, the intestinal flora provide protection for the body against gastrointestinal infections caused by pathogenic microorganisms.

When the composition of the intestinal flora is changed, as is the case, for instance, following therapeutic administration of antibiotics, various intestinal disorders may result, such as, for example, nausea, vomiting, colitis and diarrhoea.

To ameliorate these conditions, orally administrable pharmaceutical preparations containing *Bacillus subtilis* spores are normally prescribed, usually as a liquid suspension. It is intended that, upon oral administration, the spores will survive the acid environment of the stomach (pH 1 to 2) and reach the intestine (pH 6 to 8), where they will convert into vegetative forms capable of replication. However, the phenomenon of spore activation that produces the vegetative cells, being affected by the exposure to particular nutritional an chemical-physical conditions, is highly variable and depends on individual factors. Therefore it is difficult to control this phenomenon. Normally, at least one billion spores of *Bacillus subtilis* per dose are administered to ensure subsequent proliferation of a small fraction of the administered organisms in the human intestine. This approach, however, is economically wasteful and therapeutically suspect, since an unpredictable amount of live bacilli are delivered to their site of action in the intestine. Thus, there is a need in the art for methods and compositions that shield microorganisms from the gastric environment, while preserving their viability, and allow the administration of more precisely defined doses.

Other microorganisms that are administered for therapeutic purposes include lactic bacteria, e.g., *Bifidobacterium longum, Lactobacillus acidophilus, Lactobacillus bulgaricus, Streptococcus lactis, Streptococcus thermophilus,* and the like (Topley and Wilson,: *Principles of Bacteriology and Immunity,* E. Arnold, Ed., London, 1966). U.S. Pat. No. 4,946,791 describes novel strains of *Lactobacillus acidophilus* that are particularly useful due to their ability to adhere to the intestinal epithelia of different animal species.

In addition to components of the intestinal flora, enzymes that may serve important medical and/or nutritional functions may also be adversely affected by the gastric environment and/or the environment of other media wherein such enzymes may be incorporated. Examples of enzymes commonly used by the food industry are lipases, esterases, pectinases (which are used in the fruit-juice and wine industries), amylase, glucoamylase, and lactase.

Lactase, which is used in the dairy industry to hydrolyse lactose into its components glucose and galactose, also has a particular medical significance. Some individuals are "allergic" to cow's milk, and this phenomenon is related to genetic background as well as dietary habits. Milk "allergies," which appear in 40% of Asian countries and 15% of European populations, most commonly reflect lactose intolerance. This syndrome is caused by a deficiency of the enzyme β-galactosidase (lactase), which is normally secreted by epithelial cells in the small intestine. In lactase deficiency, lactose remains undigested and is not absorbed. In the small intestine, the high concentration of unabsorbed lactose draws water osmotically into the jejunum, and acts in the colon as a substrate for gas-producing coliform flora. This set of actions causes swelling and diarrhoea, which may occur from a few hours up to 12 hours after ingestion of milk. Lactose intolerance first appears at approximately ten years of age in Caucasians, and much earlier, at approximately 2–3 years, in other races in which the phenomenon is more prevalent.

Additionally, when milk is prophylactically removed from the diet of such affected individuals, even their low level of β-galactosidase production is further reduced, thus exacerbating the phenomenon of intolerance.

The phenomenon of widespread lactose intolerance has promoted the development of processes to modify or remove lactose from milk. Some of the most successful processes are based on the use of immobilized enzymes capable of fully hydrolysing milk lactose, making the milk digestible and assimilable even by lactose-intolerant individuals.

However, a drawback to the administration of biologically active compounds such as enzymes is their lability and sensitivity to environmental conditions such as pH. For instance, pancreatic lipase is completely denatured (and thus inactivated) at pH values lower than 4; conversely, the enzyme is maximally active only at pH values higher than 6.

In general, it would be predicted that enzymes sensitive to an acid environment would be ineffective when added to foods having acid pHs, such as, for instance, yoghurt and fruit juices. Furthermore, a natural barrier for products meant for nutritional administration is the gastric tract, where both the extreme acidic pH, as well as endogenous digestive enzymes, may inactivate biological food additives.

One approach to minimizing losses of active material is to encase the active compound in an enteric coating. For example, EP 583,726 teaches enterically coatable pancreatin micropellets, and JP 04 411,434 (CA 116:241966) teaches tablets containing *Lactobacillus acidophilus* coated with intestinally soluble substances. The main drawback of these teachings is related to the particle size of the preparations (pellets, tablets) which makes them unsuitable for a suspension in liquid or semiliquid foods.

U.S. Pat. No. 5,296,236 ('236 patent) describes a therapeutic system for suspension in liquid consisting of microgranules containing a pharmaceutical ingredient and coated with multiple layers of filming material that allow controlled-release of the active ingredient. The methods and compositions described in the '236 patent, however, are designed for self-contained controlled-release pharmaceutical liquid formulations and not for food additives which need not necessarily be delivered to their use point in a sustained release fashion but which must be protected from an adverse environment for extended periods of time. Furthermore, the methods and compositions are not applicable to microorganisms, which are too large to diffuse from microgranules in a manner that insures controlled-release.

It is thus an object of the present invention to provide methods and compositions that allow the addition of beneficial acid-labile or protease-sensitive biological compounds and microorganisms to ingestible materials such as foodstuffs, especially fluid and semi-fluid foods, while (a) maintaining (as long as is dictated by the particular foodstuff) the bioactivity of the compounds or organisms in an environment (either in the formulation or at the use point, or both) which is adverse to said bioactivity; and (b) creating stable suspensions of the additive(s) in ingestible materials, particularly foodstuffs, that permit administration of defined amounts of additives to consumers of foodstuffs.

The present inventor has now found that granulating and coating technology developed for the production of pharmaceutical dosage forms (as described, e.g., in the '236 patent) is particularly useful for preparing foodstuffs supplemented with microorganisms or other bioactive compounds. In particular, coated microgranules containing a biologically active material that are prepared according to the present invention are of sufficiently small size that they can be homogeneously suspended in fluid or semi-fluid foods.

SUMMARY OF THE INVENTION

It has now been found that ingestible materials such as foodstuffs which present an adverse environment for an acid-labile or protease-sensitive bioactive material such as microorganisms, peptides, polypeptides, enzymes, or vitamins can be supplemented with the bioactive material by a process comprising:

a) mixing the bioactive material with at least one excipient to form microgranules, wherein the microgranules prior to coating have a size range of 50–400 $\mu$m, a spheroidal shape, and a substantially smooth surface suitable for a uniform deposition of coating;

b) coating the microgranules with at least one coating resistant to dissolution in an acid environment, said microgranules after coating having a size within the range of 50 to 500 $\mu$M ; and c) adding a plurality of the coated microgranules produced in (b) to the ingestible material.

The enteric coating protects the microgranule contents from the milieu of the foodstuff or other ingestible material, and/or from the acid environment of the stomach. Thus, following ingestion of the foodstuff, the bioactive material within the coated microgranules remains active until after reaching the small intestine, where, due to the increase of the pH, the coating dissolves thus releasing the bioactive material.

According to the present invention, enteric-coated microgranules may be added to a variety of liquid and semi-liquid/semi-solid foodstuffs, including milk and milk products, fruit and vegetable juices, puddings, sauces, jellies, and the like. The bioactive material contained within the microgranules may comprise microorganisms, peptides, polypeptides, enzymes, vitamins, or combinations thereof, the bioactivity of which in the absence of said coating would be adversely affected by the foodstuff environment and/or the environment of the gastric tract.

In a preferred embodiment, a microgranule core comprising *Lactobacillus acidophilus* coated with an enteric film comprising cellulose acetophthalate is added to yoghurt in an amount from about 1–10% (w/w), forming a uniform stable suspension. In another preferred embodiment, the microgranule core comprises $\beta$-galactosidase, the enteric coating comprises polyacrylic esters, and the coated microgranules are added to cow's milk in an amount from about 1–10% (w/w) for human consumption. Suitable polyacrylic esters include without limitation Eudragit® S or L, or other polymers insoluble at acidic conditions (pH <6) and soluble at higher pH values.

Eudragit S® is an anionic copolymer based on methacrylic acid and methyl methacrylate. It becomes soluble in a neutral to weakly alkaline milieu by forming salts with alkali, thus affording enteric film coatings which are slowly soluble in the intestinal juice.

Eudragit L® is another methacrylic acid copolymer suitable for enteric coatings that dissolves more rapidly in the duodenum and the upper intestinal tract.

In another aspect, the present invention provides alimentary compositions comprising foodstuffs that have been supplemented with enteric-coated microgranules described above.

DETAILED DESCRIPTION OF THE INVENTION

All patents, patent applications, and references cited herein are hereby incorporated by reference in their entirety. In the case of inconsistencies, the present description, including definitions, will control.

The present invention provides methods by which a bioactive material, in particular an acid-labile or protease-sensitive bioactive compound or microorganism, can be used to supplement ingestible materials. The ingestible materials may be liquid, semi-liquid, or solid, and may comprise without limitation traditional foodstuffs or food additives. A "semi-liquid" ingestible material as used herein is one that has a viscosity that is intermediate between liquid and solid. By "enteric" is meant resistant to the acid environment of the stomach and the digestive enzymes (e.g., proteases) of the gastric environment. Thus, by use of the present invention, labile compounds such as enzymes, as well as sensitive microorganisms such as bacteria and yeast, are protected from the inactivating effects of the food in which they are suspended and/or of the adverse environment of the upper gastric tract.

As used herein, "biological activity" of the bioactive material encompasses viability (in the case of a microorganism) and metabolic activity as an enzyme, cofactor, hormone, nutritional supplement, and the like (in the case of a compound). As used herein, "viability" means the ability of a microorganism, whether a spore or a vegetative cell, to replicate and form replication-competent progeny.

In detail, the invention provides coated microgranules having sizes ranging from 50 to 500 $\mu$m, preferably from 90 to 300 $\mu$m. The coated microgranules are designed to be added to different foodstuffs, and to remain in stable suspension in fluid or semi-fluid/semi-solid foodstuffs for extended periods of time, e.g., a month or more.

The microgranule composition comprises:

a) a mixture of at least one biologically active compound or microorganism sensitive to conditions of storage or use environment (e.g., acid-labile or protease-sensitive), with or without excipients, that is treated so as to form microgranules that are substantially spherical, have a size range (before coating) of about 50–400 μm, and have other physical characteristics (described below) that ensure reproducibility and uniform distribution of the subsequent coating(s); and b) one or more successive coatings applied directly to the microgranules, at least one of which has enteric characteristics. Preferably, the microgranules after coating have a size range of 50–500 μm.

The coating may comprise a single enteric layer. Alternatively, it is possible to add one or more films of different compositions by successive applications, if indicated by the use to which the formulation will be put. Coatings having hydrophilic or hydrophobic characteristics may be applied sequentially to the microgranulate before and/or after the enteric coatings.

Bioactive compounds suitable for use in the present invention include without limitation peptides, polypeptides (preferably enzymes), and vitamins. Particularly useful enzymes include without limitation: lactase (β-galactosidase), lipase, esterase, pectinase, amylase, and glucoamylase.

Microorganisms that may be incorporated into the compositions of the present invention include, without limitation, Bacteroides, including Bifidobacteria (particularly *bifidobacterium longum*, eubacteria, and fusobacteria), *Bacillus subtilis, Lactobacillus acidophilus, Lactobacillus bulgaricus, Streptococcus lactis, Streptococcus thermophilus, E. coli* as well as, for example, all the organisms set forth in: Topley and Wilson's "Principles of bacteriology and immunity", 5th edition, Edward Arnold (publishers) ltd., London.

The microorganisms may be naturally isolated or laboratory-bred strains, and may comprise recombinant genes or be otherwise modified so as to express unique biological properties relative to their wild-type counterparts. Recombinant DNA manipulations yielding recombinant and other modified microorganisms are routinely performed using methods that are well-known in the art, as disclosed in e.g. *Molecular Cloning, A Laboratory Manual* (2nd Ed., Sambrook, et al., Cold Spring Harbor), or *Current Protocols in Molecular Biology* (Eds. Aufubel, et al., Greene Publ. Assoc., Wiley-Interscience, NY, N.Y., 1992).

Examples of recombinant microorganisms useful for supplementation of foodstuffs according to the present invention include those programmed to secrete vitamins, particularly acid-labile vitamins, specific antimicrobial substances, digestive enzymes, and the like. For example, U.S. Pat. No. 5,151,354 describes the design of microorganisms that produce amylolytic enzymes.

Excipients for use in the microgranule cores of the present invention include without limitation those commonly used in wet mixing, including dibasic calcium phosphate; sugars, such as, e.g., lactose; microcrystalline cellulose; starch; talc; and the like. The weight percentage of these compounds ranges from 10 to 80%, preferably 50–80%.

The microgranule core preparation may optionally also comprise one or more binders such as gelatin, acacia, gum tragacanth, polyvinylpyrrolidone, cellulose derivatives and the like. The weight percentage of these compounds ranges from 5 to 15%, preferably 10%.

Microgranule core preparation according to the present invention involves: a) mixing a powder containing one or more biologically active compounds and one or more granulating excipients inside a high-shear mixer-granulator; b) wetting the mixture by spraying with a granulation fluid at a set flow rate (preferably by atomizing so as to ensure a more homogeneous dispersion of the granulation fluid while the product is subject to the combined actions of the mixer and the mill); c) kneading the mixture by combined mixer-mill action; d) drying at a controlled temperature to a residual humidity of 1–10%, preferably 5–8%; and e) final screening to select granules having the desired sizes.

The mixing fluid for granulation may be water, or any other solvent which can be mixed with water, provided it is compatible with the biologically active compounds or microorganisms in the microgranulate. Examples of suitable solvents include without limitation polyethylene glycol and glycerin.

U.S. Pat. No. 5,460,828 describes effective ranges for the process parameters used in forming the microgranulate, e.g., the amount of mixing fluid relative to the dry mixture; the spray rate, the kneading time, the spray pressure, the mixer speed, and the mill speed. Useful and preferred ranges are summarized in Table 1 below.

TABLE 1

| Process parameters | I | II |
| --- | --- | --- |
| Fluid (g/Kg of product) | 80–180 | 100–150 |
| Spray rate (g/min) | 10–40 | 20–30 |
| Kneading time (min) | 5–15 | 8–12 |
| Spray pressure (bars) | 1.5–2.5 | 2 |
| Mixer speed (rpm) | 175–350 | 175–350 |
| Mill speed (rpm) | 2000–4000 | 2000–4000 |

The '193 application also describes the criteria for determining the suitability of a microgranulate for coating, e.g., the particle size distribution, aerated density, packed density, apparent density, Carr index (compressibility percentage), and the angle of repose. Useful and preferred ranges for these values are summarized in Table 2 below.

TABLE 2

| Characteristics | Acceptable | Preferred |
| --- | --- | --- |
| Mean geom. diameter ($d_g$) (μm) | 120–200 | 130–170 |
| Standard deviation ($\sigma_g$) | 1.4–2.0 | 1.5–1.8 |
| Aerated density (g/ml) | 0.4–0.7 | 0.50–0.66 |
| Packed density (g/ml) | 0.5–0.9 | 0.55–0.80 |
| Apparent density (g/ml) | 1.2–1.5 | 1.30–1.45 |
| Carr index (%) | 5–15 | 6–12 |
| Angle of repose (°) | 20–40 | 26–30 |

In addition, the observations of shape and surface made by electron microscopy and stereomicroscopy are also taken into account. Preferably, microgranules before coating have a spheroidal shape and a smooth surface substantially free of roughness.

According to the invention, the granulate, screened as appropriate and having suitable size and surface characteristics, is then coated with an enteric coating. The enteric coating, by definition, is one that is relatively resistant to dissolution in an acid environment, such as that of common foods such as yoghurt (pH~4) or of gastric juices (pH=1–2). An effective enteric coating for a bioactive compound-containing microgranulate preserves from about 70% to about 100% of the activity of the compound during the intended shelf-life or usage interval of the foodstuff to which it is added. Furthermore, an effective enteric coating preserves from about 70% to about 100% of the activity of the compound following ingestion of the foodstuff to which it is added. Similarly, an effective enteric coating for a microorganism-containing microgranulate preserves the viability of from about 70% to about 100% of the microorganisms that are contained within the microgranules during the intended shelf-life or usage interval of the foodstuff to which it is added, and preserves the viability of from about 70% to about 100% of the microorganisms following ingestion.

It will be understood that each supplemented foodstuff prepared according to the present invention can be evaluated with respect to the stability of the biologically active material contained therein, using methods well known in the art suitable for the quantitation of each biologically active material. For example, when the foodstuff additive is a microorganism, the viability of the microorganism is assessed at different times after supplementation using the colony method described in Example 8 below. When the material is an enzyme or other protein, stability is evaluated using an enzymatic assay, immunoassay, or combinations thereof. Finally, when the material is a vitamin or other compound, an appropriate detection method is selected based on chemical and/or spectral characteristic of the compound. By comparing the percentage of bioactive material remaining in the foodstuff as a function of time after supplementation, a rate of inactivation can be calculated. This value, in turn, allows the calculation of the amount of the bioactive material that must be added to the foodstuff in order to provide a predetermined and reproducible level of active material during the predicted use interval of the foodstuff.

Substances for use in the enteric coating that are capable of endowing the microgranules with enteric properties include without limitation cellulose acetophthalate (CAP), hydroxypropyl methyl cellulose phthalate (HPMCP), polyacrylic esters (such as, e.g., Eudragit-L and S), and combinations thereof. Plasticizers may also be included in the enteric coating layer; these include without limitation diethyl phthalate, dibutyl sebacate, triacetin, trialkyl citrates, vegetable oils, polyethylene glycol, propylene glycol, and combinations thereof. Preferred plasticizers include diethyl phthalate and polyethylene glycols. In a preferred embodiment, a solution is prepared containing, for example, CAP, Eudragit-L, or HPMCP in a proportion of 4–10% (w/w). Optionally, a plasticizer, for example, diethylphthalate, is added in a proportion of 1–10% (w/w). These substances are dissolved in a solvent system that may comprise water, or organic solvents, such as, for example, acetone, isopropyl alcohol, chloroform, or mixtures thereof. The dissolved coating materials are then applied to the microgranulate. The filming step is preferably carried out in a fluid-bed apparatus using the well-known Wurster process, in which filming materials maintained in solution are applied to the microgranules. Details of the air suspension coating technique can be found in D.Jones, *Drug Development and Industrial Pharmacy* 20: 3175–3206 (1994).

Applications

The methods and compositions of the present invention can be used to provide foodstuffs supplemented with bioactive compounds or microorganisms that provide nutritional or medical benefit.

Foodstuffs that can be supplemented with the enteric compositions of the present invention include without limitation milk and milk products. The milk may be whole milk or low-fat milk, and may be derived from any commonly available species, e.g., cows, sheep, or goats. Examples of milk products that may be supplemented according to the present invention include without limitation cheese, cream, ice cream, yogurt, frozen yogurt, other milk or milk-containing products such as frozen desserts, and the like. A preferred food for supplementation with Lactobacillus is yoghurt made of cow's milk; while a preferred liquid for supplementation with lactase is whole or low-fat cow's milk. In both applications, the coated microgranules are preferably added to milk in an amount of from about 1 to about 106 (w/w).

It will be understood that other foodstuffs, including liquids and semi-liquid/semi-solid foods, may also be used in practicing the present invention. These include without limitation: fruit juice (including citrus juices), fruit-based sauces and jellies, puddings, and the like.

The methods, tables and examples provided below are intended more fully describe preferred embodiments of the invention and to demonstrate its advantages and applicability without limiting its scope.

EXAMPLE 1

Preparation of Microgranules Containing β-galactosidase

A mixture containing 100 g of β-galactosidase (Fluka Chemika-Biochemika, Buchs, Switzerland), 1,340 g of calcium phosphate and 150 g of polyvinylpyrrolidone was mixed for 5 minutes in a Fielder P10 kneader so as to ensure a satisfactory degree of homogeneity. Two hundred ml of water atomized at a pressure of 2 bars were then added to the stirred mixture at a rate of 10 ml/min. The granulate was mixed for 10 more minutes to promote the formation of spherical microgranules. The product was then dried for about 2 hours on a static bed at a controlled temperature of 35° C. until the residual humidity of the preparation was reduced to a value of 4 to 5% by weight. The microgranulate was then screened through 0.6 mm sieves to give a granulate having a particle size range of from 90 to 300 $\mu M$ and a spheroidal shape substantially free of any surface roughness or unevenness. The granulate portions with sizes smaller than 90 $\mu m$ or larger than 300 $\mu m$ were separated, milled, and re-used in subsequent manufacturing cycles.

EXAMPLE 2

Preparation of Microgranules Containing *Lactobacillus acidophilus*

A) A mixture containing 2,100 g of lyophilized powder of *Lactobacillus acidophilus* 601 (Wiesby GmbH & CoKG), 500 g of polyvinylpyrrolidone and 1,500 g of lactose was mixed for 5 minutes so as to ensure satisfactory homogeneity. Five hundred ml of water atomized at a pressure of 2 bars were then added to the stirred mixture in a nitrogen environment at a rate of 35 ml/minute. The granulate so obtained was mixed for a further 15 minutes to promote the formation of spherical microgranules. The microgranular product was dried in vacuo for 1 hour on a static bed at ambient temperature up to a steady residual humidity, i.e., when there is no further reduction in weight. After drying, the granulate was screened through 0.6 mm sieves to give a granulate with a particle size distribution ranging from 90 to 300 $\mu m$, and spheroidal shape lacking superficial unevenness. The portions outside the particle size range were milled again and re-used in subsequent granulations.

B) A mixture containing 375 g of lyophilized powder of *Lactobacillus acidophilus* 601 (Wiesby GmbH & CoKG), 375 g of polyvinylpyrrolidone, and 3,000 g of lactose was mixed for 5 minutes. 250–280 ml of water atomized at a pressure of 2 bars were then added to the stirred mixture in a nitrogen environment at a rate of 25 ml/minute. The granulate so obtained was mixed for a further 10 minutes to promote the formation of spherical microgranules. The microgranular product was dried in vacuo for 1 hour in a oven at 30° C. After drying, the granulate was screened to give a particle size distribution ranging from 90 to 300 µm.

EXAMPLE 3

Preparation of Microgranules Containing *Bifidobacterium longum*

1,200 parts of 450-mesh lactose, 300 parts of polyvinylpyrrolidone, and 100 parts of lyophilized *Bifidobacterium longum* (DIFCO-Milan) were combined and mixed in a Turbula apparatus for 10 minutes. The resulting mixture was then transferred to a high-speed mixer/granulator, and 200 ml of water atomized at a pressure of 1 bar were added at a rate of 20 g/minute. The granulate so obtained was kneaded for an additional 10 minutes at a speed of 175 rpm to promote the formation of spherical microgranules. The microgranulate was then dried for 2 hours in a static oven at a temperature of 35° C. After drying the granulate was screened to separate the particle size fraction ranging from 100 to 300 µm.

EXAMPLE 4

Coating of Microgranule with Cellulose Acetophthalate (CAP)

Table 3 (below) shows the composition of seven different formulations containing cellulose acetophthalate that can be used for coating microgranules containing biologically active compounds.

TABLE 3

| INGREDIENTS (% w/w) | A | B | C | D | E | F |
|---|---|---|---|---|---|---|
| Cellulose acetophthalate | 4 | 5 | 7 | 6 | 11 | 10 |
| Acetone | 75 | 50 | — | 40 | — | 45 |
| Ethyl acetate | — | — | 45 | — | 40 | — |
| Isopropyl alcohol | 20 | 44 | 45 | 40 | 40 | 40 |
| Diethyl phthalate | 1 | 1 | 3 | 2 | 4 | 2 |
| Talc | — | — | — | 10 | 5 | 2 |

Formulation A is preferred for coating the microgranules described in Example 1.

To prepare these solutions, acetone, isopropyl alcohol, and cellulose acetophthalate are mixed in a 3-liter flask and heated to 40° C. Diethyl phthalate is then added. After complete dissolution, the solution is cooled and applied to the microgranulates prepared as described in Example 1.

EXAMPLE 5

Formulation of Coatings Containing Eudragit L®

Table 4 below shows the composition of four different formulations (G to J) containing polyacrylic esters (Eudragit L®, 12.5% solution in isopropanol, Rohm Pharma GMBH, Darmstadt, Germany) that can be used for coating microgranules containing microorganisms.

TABLE 4

| INGREDIENTS (% w/w) | G | H | I | J |
|---|---|---|---|---|
| Eudragit L sol. 12.5% | 5 | 7.05 | 8.75 | 4.37 |
| Acetone | 30 | 20 | — | 25 |
| Isopropyl alcohol | .05 | .07 | 20 | .04 |
| Diethyl phthalate | 10 | 5 | — | 5 |
| Talc | — | — | 5 | 10 |
| Castor oil | — | — | 5 | — |

Formulation H is preferred for coating the microgranules prepared as described in Example 2.

EXAMPLE 6

Formulations of Coatings Containing Hydroxypropyl Methyl Cellulose Phthalate (HPMCP)

A film was prepared having the following weight percent composition (w/w):

| HPMCP | 8% |
|---|---|
| Ethanol | 46% |
| Dichloromethane | 46% |
| Myvacet | 0.6% |

(HPMCP is from Shin Ester Chemical Co.; Myvacet, a plasticizer made up of partially hydrogenated monoglyceride acetilate, is from Eastman.)

When applied in a range of 5 to 70% (w/w) dry film per granule, this coating is particularly effective to coat microgranules containing pancreatic enzymes. That is, the enzymes remain stable in the acid environment of the stomach; furthermore, they are released into the pylorus at the same time as the food to which the microgranulate had been added.

EXAMPLE 7

Application of Filming Solutions

Two kg of microgranular preparation prepared as described in Examples 1, 2, and 3 were loaded into a Glatt apparatus equipped with a 7" Wurster insert for fluid-bed filming. Air at a temperature of 30 to 35° C. was blown into the apparatus at a rate of 40 to 45 m³/hour. For CAP-containing mixtures (see Example 4), 2,200 ml of solution were used; for Eudragit L containing mixtures, (see Example 5), 1,100 ml were used; and for HPMCP containing mixtures (see Example 6), 900 ml where used. The solutions were sprayed at a pressure of 2 bars and at a rate of 8–10 g/minute.

EXAMPLE 8

Testing for Gastric Resistance for *Lactobacillus acidophilus*

The gastric resistance test was carried out using the six-vessel apparatus described by USP XXII Ed. page 1580, operating at 37° C. and 60 rpm in 750 ml of 0.1 N HCl. Samples were taken after the first and second hours. Microgranules prepared as described in Example 1 A) and coated as described in Example 4 (formulation a) and in Example 7 were used. The bacterial count was carried out according to the following plate method. Plates were prepared using culture medium formulated as follows: 20.0 g of tryptone; 5.0 g of yeast extract; 20.0 g of cellobiose; 4.0 g of sodium chloride; 1.5 g of sodium acetate trihydrate; 0.5 g of Tween 80; 1.0 g of esculin; 0.5 g of ammonium iron (III) citrate; 6.5 ml of a 0.2% red chlorophenol solution (obtained by suspending 0.2 g of red chlorophenol in few ml of absolute ethanol and filling to 100 ml with distilled water); and 15.0 g of agar-agar in 1000 ml of distilled water were dissolved by steaming and filled into 80-ml bottles and sterilized in an autoclave at 121° C. for 15 min. After pouring, the pH was 6.6 and the colour was light reddish lilac. Cell counts were determined by applying the pour-plate method using about 10 ml per petri dish (9 cm diameter) and incubating for 48 hours at 40° C. under CO2 atmosphere in anaerobic jar.

In all of the samples tested, the fraction of bacteria released into solution did not exceed 10%, thus meeting the primary USP criterion for gastric resistance. Furthermore, at the end of treatment, the number of live cells per 1,000 mg of microgranulate was less than 100 in the control microgranulate (not enteric) as compared to $2 \times 10^8$ of the enteric-coated microgranulate. The starting amount of cells contained in each microgranulate was: 4.4 $10^9$ cells per gram.

Since the acid conditions used in the gastric resistance test are quite extreme, the resistance to dissolution of the enteric-coated Lactobacillus-containing microgranules demonstrated in this test indicates that the microgranules will remain intact in less stringent acid conditions, such as those found, e.g., in yoghurt.

EXAMPLE 9

Testing for Microgranulate Suspension

The following experiment was performed to test the microgranulate suspendibility in various alimentary fluids. A microgranulate having an average size of 100 to 300 µm (prepared as described in Example 2 B) and coated as described in Example 4 (formulation A) and, as reference preparations, uncoated lactose microspheres sized 500–800 µm and 2,000 µm, were suspended in food vehicles of different densities using the following procedure. 500 mg of granulate and 10 ml of vehicle were transferred to a graduated centrifuge tube and stirred for 15 seconds on a horizontal agitator. The sedimented percentage of granules was then determined at pre-established times by observing single samples against the light. The following commercially available foods were used as vehicles: A) DANONE yoghurt diluted 1:5; B) ZUEGG orange juice; C) VALNEVE UHT milk, partially skimmed. The results are shown in Table 5.

TABLE 5

| | % of granulate sedimented in time | | | | | | | | | | | |
|---|---|---|---|---|---|---|---|---|---|---|---|---|
| | 100–300µ | | | | 500–800µ | | | | 2,000µ | | | |
| | 5s | 10s | 30s | 60s | 5s | 10s | 30s | 60s | 5s | 10s | 30s | 60s |
| A | 0 | 10 | 30 | 60 | 50 | 100 | — | — | 100 | — | — | — |
| B | 0 | 30 | 70 | 100 | 100 | — | — | — | 100 | — | — | — |
| C | 0 | 30 | 50 | 100 | — | — | — | — | 100 | — | — | — |

After 5 seconds, there was no sign of sedimentation of the 100–300 µm microgranular composition in any of the three vehicles. By contrast, almost all of the reference compositions were almost completely sedimented. This illustrates the strong tendency of the composition of the present invention to form a sufficiently stable suspension in liquid and semi-liquid foods.

EXAMPLE 10

Preparation of Yoghurt Containing Enteric-coated *Lactobacillus acidophilus* Microgranules

*Lactobacillus acidophilus* microgranules prepared as in Example 2 A) and coated with an enteric coating as in Example 5 were added to the yoghurt prepared in accordance with the procedure described below. Cow's milk with a fat content of 1 to 5% was heated to about 82° C. and maintained under these conditions for 30 minutes. After homogenization, the milk was cooled to 43–46° C. and inoculated with 2% (v/v) of a culture containing *Lactobacillus bulgaricus* and *Streptococcus thermophilus*. The milk was then incubated at 43° C. for 3 hours and cooled to a temperature lower than or equal to 4.4° C. The cooled product showed a measurable acidity of 1–1.2% and a pH of 4.3–4.4. The enteric-coated *Lactobacillus acidophilus* microgranulate (10 g) was then added to the yoghurt mass (1,000 g) by stirring until a homogeneous 1% dispersion was achieved. The product obtained stored at 4° C. showed a stability longer than one month. The stability was tested by bacterial count according to the method described in Example 8.

EXAMPLE 11

Preparation of Milk Containing Enteric-coated β-galactosidase Microgranules 750 mg of a β-galactosidase-containing microgranulate prepared as described in Example 1 and coated with cellulose acetophthalate as described in Example 4 contain the equivalent of 50 mg of β-galactosidase. Given a specific enzymatic activity of 30,000 NLU/g, this amount of enzyme (corresponding to 1,500 NLU) is sufficient to digest the lactose contained in one liter of milk. This amount of coated microgranulate is mixed with one liter of milk for 10–15 seconds to form a homogeneous suspension.

What is claimed is:

1. A method for preparing an ingestible product comprising a suspension of a bioactive material wherein the ingestible product is liquid or semi-solid and constitutes an environment adverse to the activity or viability of said bioactive material, said method comprising the steps of:
   (a) forming microgranules from a mixture of the bioactive material and at least one excipient, said microgranules prior to coating in step (b) below having a size range of 50–400 µm, a spheroidal shape, and a substantially smooth surface suitable for coating;
   (b) rendering the coated microgranules resistant to chemical attack by the adverse environment of said ingestible material by coating the microgranules with at least one coating resistant to dissolution in an acid environment, said acid environment including gastric fluid, said coated microgranules having a size within the range of 50–500 µm; and
   (c) suspending said coated microgranules to the ingestible material, thereby forming a suspension of distinct coated microgranules in said material, said coated microgranules remaining in said ingestible product throughout the shelf life of said product and until its consumption.

2. The method of claim 1, wherein the ingestible material is a foodstuff.

3. The method of claim 2, wherein the foodstuff comprises a liquid selected from the group consisting of milk, fruit juice, vegetable juice.

4. The method of claim 1, wherein the bioactive material retains at least 70% of its biological activity during the usage interval of the ingestible material, and retains at least 70% of its biological activity following ingestion thereof.

5. The method of claim 1, wherein the bioactive material is selected from the group consisting of acid-labile materials, protease-sensitive materials, or combinations thereof.

6. The method of claim 5, wherein the bioactive material is selected from the group consisting of microorganisms, peptides, polypeptides, enzymes, vitamins, and combinations thereof.

7. The method of claim 6, wherein said microorganisms are selected from the group consisting of *Bifidobacterium longum, Lactobacillus acidophilus, Lactobacillus bulgaricus, Streptococcus lactis, Streptococcus thermophilus,* and *E. coli.*

8. The method of claim 7, wherein said microorganism is *Lactobacillus acidophilus.*

9. The method of claim 7, wherein said microorganisms comprise recombinant genes.

10. The method of claim 6, wherein said polypeptides are enzymes selected from the group consisting of lactases, amylases, glucoamylases, lipases, esterases, pectinases.

11. The method of claim 10, wherein said lactase is β-galactosidase.

12. The method of claim 1, wherein said excipient is selected from the group consisting of dibasic calcium phosphate, sugars, microcrystalline cellulose, starch, talc and lactose, polyvinylpyrrolidone, gelatine, acacia, cellulose derivatives, and combinations thereof.

13. The method of claim 1, wherein said coating comprises a material selected from the group consisting of cellulose acetophthalate, polyacrylic esters, hydroxypropyl cellulose phthalate, and combinations thereof.

14. The method of claim 13, wherein said coating further comprises a plasticizer selected from the group consisting of diethyl phthalate, dibutyl sebacate, triacetin, trialkyl citrates, vegetable oils, polyethylene glycol propylene glycol, and combinations thereof.

15. The method of claim 1, wherein said mixing step is carried out in a fast kneader/granulator, and said coating step comprises the Wurster process carried out in a fluid-bed apparatus.

16. The method of claim 1, wherein the bioactive material is β-galactosidase; the excipient comprises calcium phosphate and polyvinylpyrrolidone; and, the microgranules are coated with a mixture of cellulose acetophthalate and diethyphthalate.

* * * * *